United States Patent [19]

Smith

[11] Patent Number: 5,665,893

[45] Date of Patent: Sep. 9, 1997

[54] REFERENCE BLOCK FOR DETERMINING OPERATING CHARACTERISTICS OF ULTRASONIC TRANSDUCER IN RIGHT CIRCULAR CYLINDER TYPE PROBE

[75] Inventor: Thurman Dale Smith, Richland, Wash.

[73] Assignee: General Electric Company, San Jose, Calif.

[21] Appl. No.: 660,613

[22] Filed: Jun. 6, 1996

[51] Int. Cl.$^6$ .................................................. G01N 29/00
[52] U.S. Cl. ........................................................... 73/1.82
[58] Field of Search ....................................... 73/1 DV, 13

[56] References Cited

U.S. PATENT DOCUMENTS

| | | | |
|---|---|---|---|
| 4,309,904 | 1/1982 | Jones et al. | 73/1 DV |
| 4,331,021 | 5/1982 | Lopez et al. | 73/1 DV |
| 4,475,376 | 10/1984 | Keilman | 73/1 DV |
| 4,964,295 | 10/1990 | Nottingham et al. | 73/1 DV |

FOREIGN PATENT DOCUMENTS 502313  7/1977  U.S.S.R. .................. 73/1 DV

*Primary Examiner*—Robert Raevis
*Attorney, Agent, or Firm*—James E. McGinness; Dennis M. Flaherty

[57] ABSTRACT

A reference block for determining the characteristics of individual ultrasonic transducers contained within right circular cylinder type ultrasonic probes. Right circular cylinder type ultrasonic probes are designed for performing ultrasonic inspections of components that can only be examined from within a center line access hole. The reference block is made from the same material as that of the right circular cylinder type components which will be examined using the ultrasonic probe being characterized and is designed with curved contact surfaces that specifically duplicate the surfaces of those components. This reference block can be used to calibrate instruments prior to contact inspection using angle-beam search units. The reference block is also useful for checking the performance of both angle-beam and straight-beam search units and for evaluating instrument performance.

20 Claims, 8 Drawing Sheets

REFERENCE BLOCK FOR DETERMINING OPERATING CHARACTERISTICS OF ULTRASONIC TRANSDUCER IN RIGHT CIRCULAR CYLINDER TYPE PROBE

FIELD OF THE INVENTION

This invention relates generally to non-destructive examination (NDE) of material, such as metal or alloy, for voids, flaws, cracks and other defects that can be detrimental to the integrity of the material. Specifically, the invention relates to calibration of ultrasonic transducers used to inspect parts and components.

BACKGROUND OF THE INVENTION

Ultrasonic examinations are performed within the nuclear industry and other industries to determine the condition of parts and components. The metal or alloy material of a part or component is inspected using ultrasound to detect any flaws which could prove detrimental to the safe operation of that part or component. The ultrasonic NDE method can be used to detect internal flaws in most engineering metals and alloys. Bonds produced by welding, brazing, soldering and adhesive bonding can also be ultrasonically inspected.

Ultrasonic inspection is used for quality control and materials inspection in the fabrication of structures, reactor pressure vessels, airframes, pipe systems, bridges, motor vehicles and jet engines. The present invention has application in all of these fields.

For successful application of ultrasonic examination techniques, the ultrasonic system, including transducers, must be suitable for the type of inspection being performed. If the proper transducer is not used, there is a high potential for gross error in the inspection results, or there could be no results at all. For instance, using a common ultrasonic transducer that has a hard flat-surfaced Lucite wedge for examining as-welded overlaid pipe welds causes gross errors in the ultrasonic inspection results. In many cases ultrasonic inspection data is not recorded at all. This is due to the presence of air gaps between the transducer head and the rough surface being inspected, which air gaps form an opaque barrier.

Ultrasonic characterization of cracks in materials is at least a two-step process: 1) detection and location; and 2) sizing in absolute or relative terms. In accordance with the first step of this process, the transducer is excited to emit an ultrasonic wave which is coupled to the structure being inspected. The emitted wave enters the structure, where it is reflected by the crack. The return path of the reflected wave impinges on the transducer, where it is detected as a "pulse echo" signal.

The determination of the crack size, or depth of penetration in the case of surface-connected flaws, is a different and more complicated task. A conventional method for determining the depth of penetration of a planar crack is the back-scattered time-of-flight technique. This method takes advantage of the backward scattering of waves of ultrasonic energy at the edges of a crack. An emitter of short pulses of ultrasound, coupled to the inspection surface, causes refracted sound waves to impinge on the crack edge, which scatters the ultrasonic energy in all directions. A detector situated on the same or opposite surface as the crack is excited by scattered pulsed energy after a time delay. The time delay is a function of the crack height, the angle of refraction and other dimensions. By measuring the time-of-flight for the round trip from the transducer to the crack edge and back to the transducer, the crack height can be easily computed from the geometry.

Such ultrasonic inspections of the structural integrity of industrial components made of steel and other metals depend upon knowing the beam profiles of the ultrasonic waves that propagate into these components. It is common practice to control the refracted angle of the ultrasound by using hard shoes that follow the surface and maintain, more or less, a constant angle. Surfaces that are rough, with both short-term and long-term roughness, pose a problem because it is difficult to maintain contact. In addition, anisotropic materials, such as stainless steel weld metal and cast stainless steel components, redirect the ultrasound inside the material in an unpredictable manner.

Rough surface conditions and anisotropic grain structure can result in unpredictable results using conventional examination methods. The angle of refraction of an ultrasonic transducer in a probe having a flat contact surface is measured on a special calibration block, and then it is assumed that the angle is the same when applied to a specimen. The angle of refraction within a given material is controlled by the ultrasonic transducer's angle of incidence, i.e., the number of degrees by which the path of propagation is tilted relative to an axis normal to the object surface. The angle of incidence is determined in accordance with Snell's Law, which can be expressed mathematically as:

$$\sin a/\sin b = V_1/V_2$$

where a is the angle of incidence; b is the angle of refraction; $V_1$ and $V_2$ are the respective wave velocities in the first and second media. Snell's Law describes wave behavior at an interface between two different media. The law applies even if mode conversion occurs.

Right circular cylinder type ultrasonic probes are used within the nuclear industry to perform inspections of components such as main recirculation pump shafts, head hold down studs, incore housings, stub tube to control rod drive housings and various other right circular cylinder type components. Standard ultrasonic transducer reference blocks currently used within the ultrasonic industry have flat contact surfaces and are designed for contact transducers that also have flat contact surfaces. Thus, there is a need for a standard ultrasonic transducer reference block which can be used to determine the operating characteristics of ultrasonic transducers contained within right circular cylinder type probes.

Standard reference blocks are used by the nondestructive testing industry mainly to calibrate instruments prior to contact inspection using angle-beam search units. These blocks are also useful for checking the performance of both angle-beam and straight-beam search units and for evaluating instrument performance.

Common ultrasonic reference standards such as the International Institute of Welding (IIW) type 1 block and the miniature angle beam block, a derivative of the IIW block, and various other rectangular or flat reference blocks have flat contact surfaces. These common reference blocks are designed specifically for applying flat-surfaced contact transducers and therefore are not applicable for right circular cylinder type probes that have curved transducer contact surfaces.

SUMMARY OF THE INVENTION

The invention is a reference block for determining the characteristics of individual ultrasonic transducers contained within right circular cylinder type ultrasonic probes. Right circular cylinder type ultrasonic probes are designed for performing ultrasonic inspections of components that can only be examined from within a centerline access hole, such as main recirculation pump shafts, head hold-down bolts, incore monitor housings and welds, stub tube to control rod drive housing welds, control rod drive housings, and various other components of similar design. The reference block of the invention is made from the same material as that of the right circular cylindrical components which will be examined using the ultrasonic probe being characterized and is designed with curved contact surfaces that specifically duplicate the surfaces of those components. This reference block can be used to calibrate instruments prior to contact inspection using angle-beam search units. The reference block is also useful for checking the performance of both angle-beam and straight-beam search units and for evaluating instrument performance.

DETAILED DESCRIPTION OF THE PREFERRED EMBODIMENTS

Figure 1:
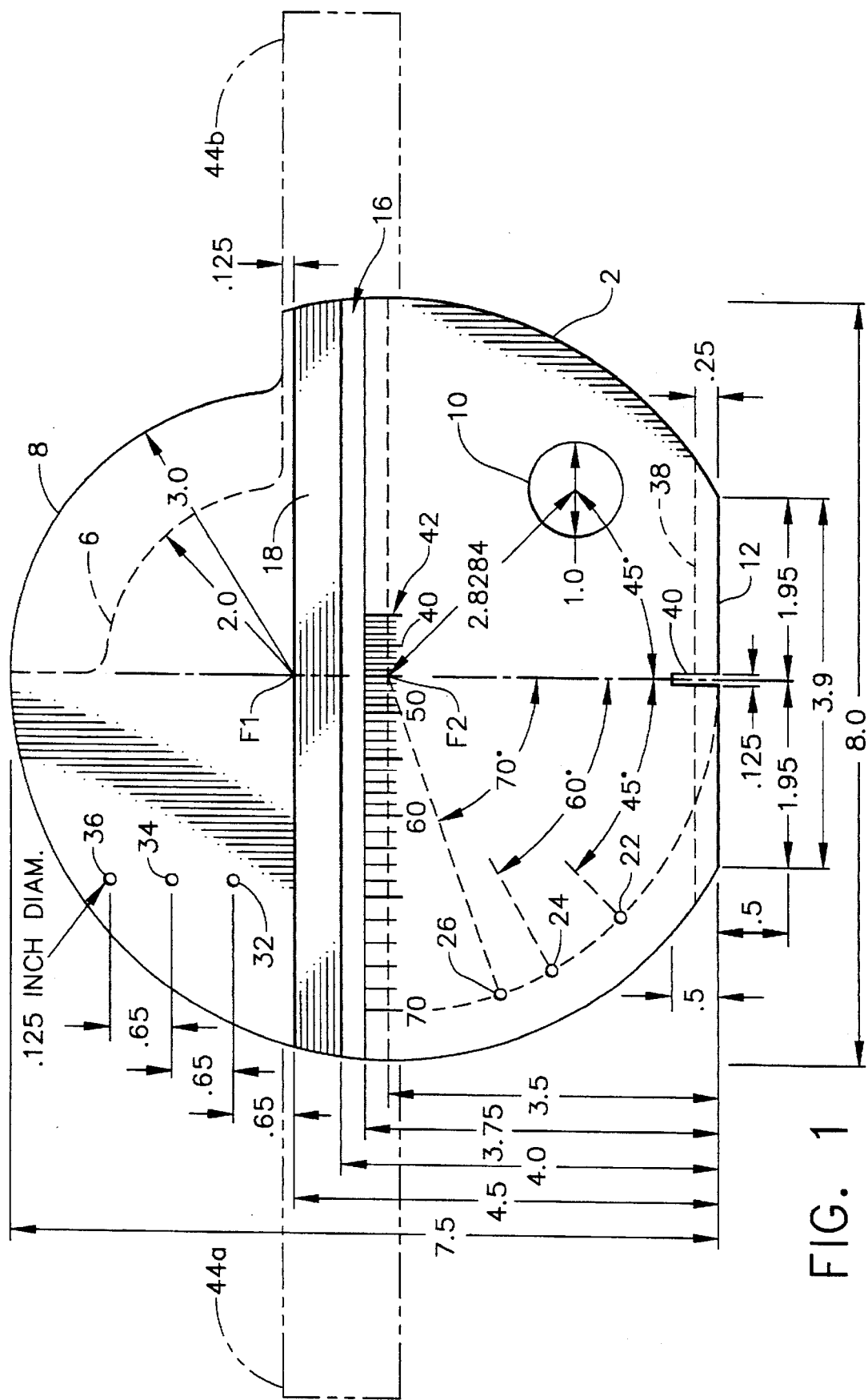
FIG. 1 is a schematic diagram showing a front view of the reference block in accordance with a preferred embodiment of the invention.
Figure 2:
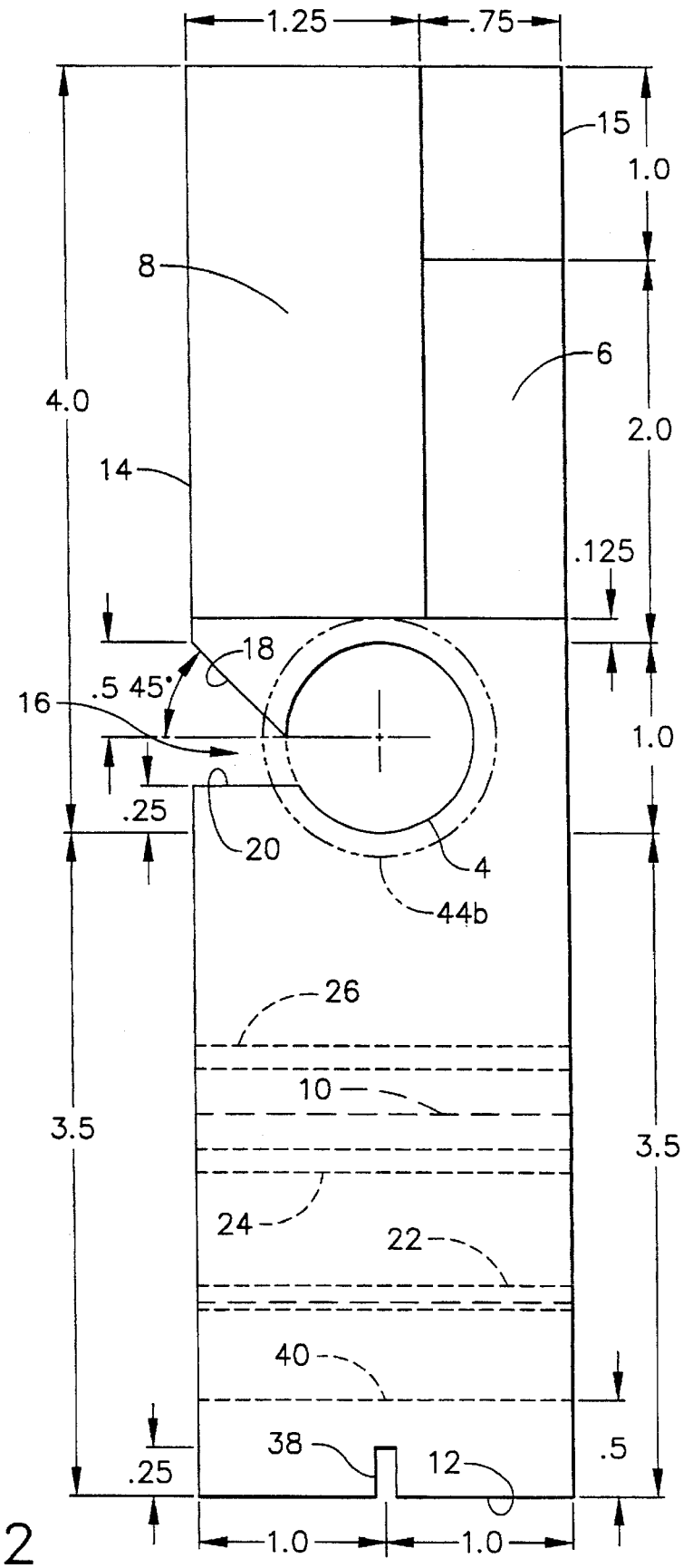
FIG. 2 is a schematic diagram showing a side view of the reference block in accordance with a preferred embodiment of the invention.
Figure 3:
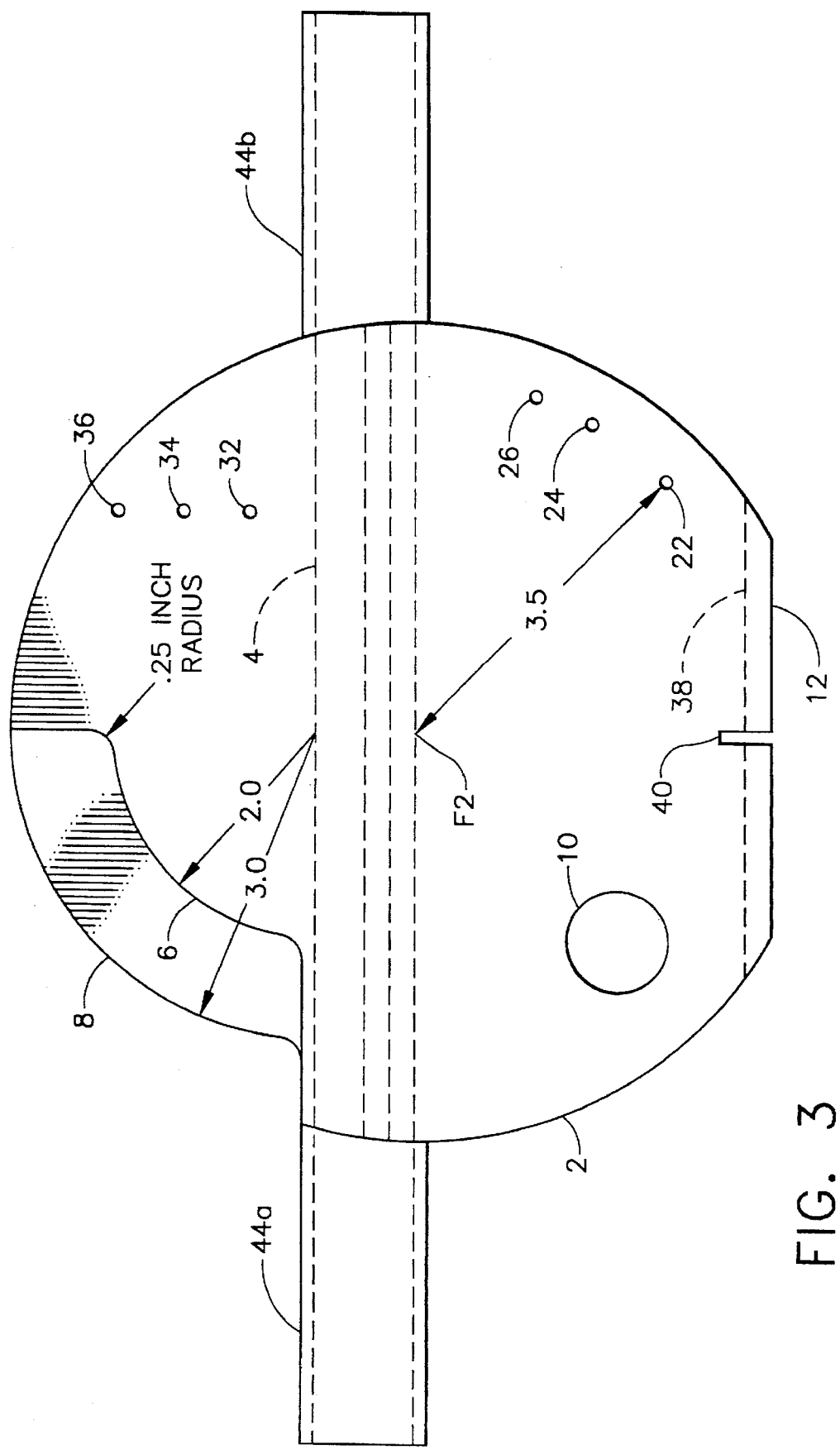
FIG. 3 is a schematic diagram showing a rear view of the reference block in accordance with another preferred embodiment of the invention.

The ultrasonic reference block design concept of the present invention is illustrated in FIGS. 1–3. The reference block 2 is basically a right circular cylinder with a diameter of eight inches with special features machined into it. An ultrasonic reference block in accordance with the invention can be derived from any appropriate solid right circular cylinder and of any size and type of metal. The material type used for the block must be of a type that corresponds to the material that will be examined with the ultrasonic probe that is to be characterized using the reference block of the invention. The preferred embodiment disclosed herein is fabricated from Type 304 stainless steel. However, the reference block can be made from any material that supports ultrasound characteristics.

The special features described herein for this type and size of material are applicable for all sizes of ultrasonic reference blocks and ultrasonic probes. This disclosure describes the characterization of transducers contained within an ultrasonic probe developed for the inspection of boiling water reactor main recirculation pump shafts. Each piezoelectric transducer incorporated in the probe must be calibrated separately using the present invention.

Figure 6A:
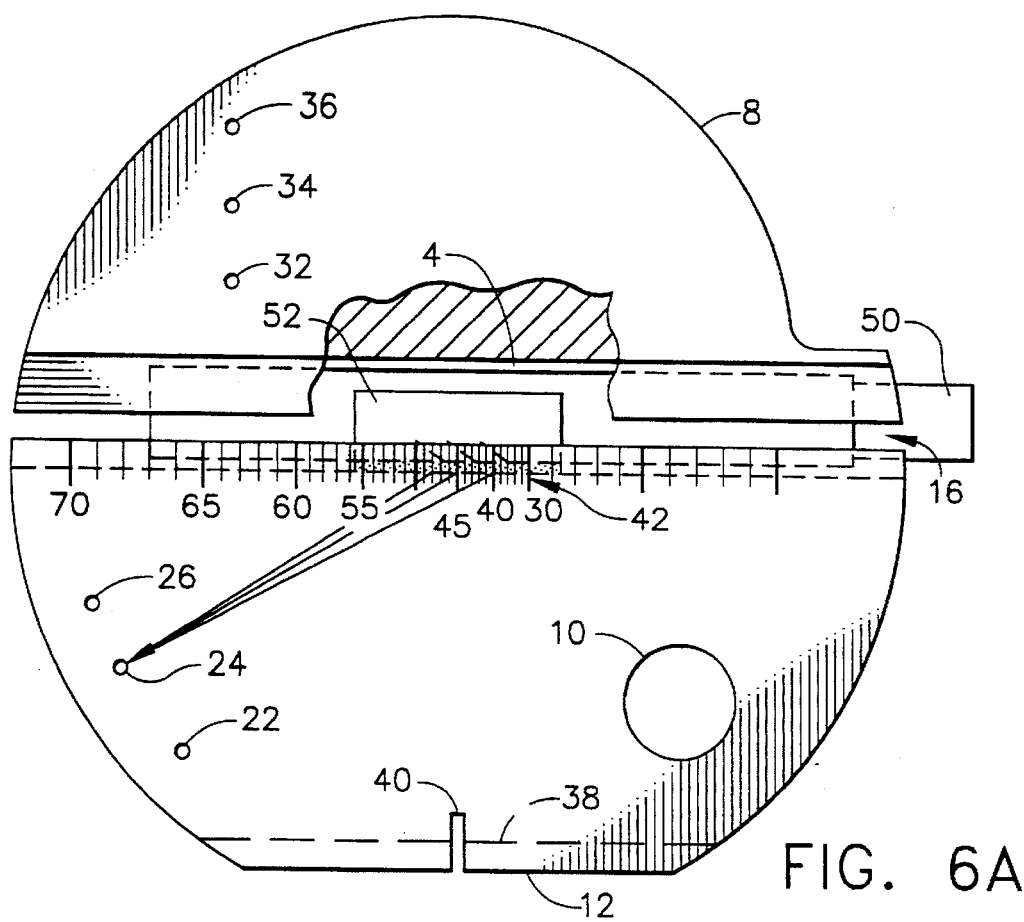
FIG. 6A is a schematic diagram showing a front view of the reference block shown in FIG. 1 with a right circular cylinder type ultrasonic probe inserted in the access hole at a position which enables individual transducer beam spread determination.
Figure 6B:
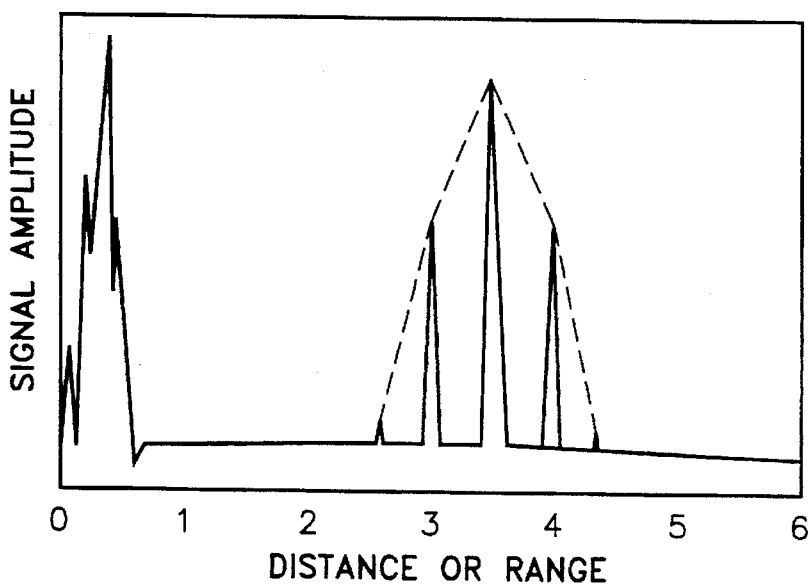
FIG. 6B is a schematic depiction of an ultrasonic instrument display of signal amplitude vs. sweep range for signals transmitted from an ultrasonic transducer positioned as shown in FIG. 6A and returned from a side-drilled circular hole at the 60° position in the reference block.
Figure 6C:
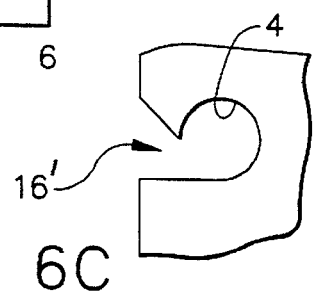
FIG. 6C is a schematic diagram showing a side view of an access hole machined into the reference block in accordance with a further preferred embodiment of the invention.

The block 2 has a planar base 12, a front planar face 14 perpendicular to base 12, a rear planar face 15 parallel to face 14, and a circular cylindrical access hole 4 machined into the block and oriented parallel to the base 12 and parallel to the front and rear faces. The probe is inserted into the access hole 4 from the side (see FIG. 2). The front face 14 of block 2 has a window 16 machined therein which runs the length of and communicates with the access hole 4. The window 16 is bounded by a planar surface 18 which lies parallel to the centerline axis of access hole 4 and at a 45° angle with respect to the planar base 12, and by a planar surface 20 which lies parallel to the planar base 12. A window 16' having an alternative geometry is shown in FIG. 6C. Probe access holes of any size may be used based solely on the diameter of the ultrasonic probe.

The ultrasonic reference block shown in FIGS. 1–3 typifies the inventive concept for all sizes of right circular cylinder type reference blocks, but all of the special features may be altered to make the block applicable for other right circular cylinder type component designs. Exemplary dimensions are given in inches for a specific embodiment designed to calibrate an ultrasonic probe used to examine Type 304 stainless steel BWR main recirculation pump shafts. The diameter may be sized for the applicable component size to be examined. The centerline access hole 4 may be sized for the probe diameter to be employed.

One special feature comprises the provision of two circumferential reflecting surfaces 6 and 8, located in the same quadrant of the reference block, for calibrating the ultrasonic instrument's sweep range and, simultaneously, determining the transducer's index point. The reflecting surfaces 6 and 8 are sections of circular cylinders of different radii having a common center of curvature located at a top focal point F1. Reflecting surface 6 has a radius of 2.00 inches; reflecting surface 8 has a radius of 3.00 inches. The radii are measured from focal point F1. The focal point F1 and the reflecting surfaces 6 and 8 are used to determine the central ray exit point of each transducer (i.e., the transducer index point) and to calibrate the ultrasonic instrument's baseline sweep for a given material type.

Another feature of the ultrasonic reference block of the invention is a one-inch-diameter hole 10 that penetrates through the block's cross section. After an angle beam transducer's index point has been determined, its beam angle can then be derived by referencing this one-inch-diameter hole.

A third feature of this block is the use of 0.125-inch side-drilled holes 22, 24 and 26 that may be used to determine a transducer's beam spread. These holes are positioned at 0°, 45°, 60° and 70° for this reference block concept. The centers of holes 22, 24 and 26 lie along an arc centered at a bottom focal point F2. A second set of 0.125-inch side-drilled holes 32, 34 and 36 are arranged in a line perpendicular to the planar base 12. Holes 32, 34 and 36 are used for determining distance amplitude corrected (DAC) curves. In accordance with the preferred embodiment, each of holes 22, 24, 26, 32, 34 and 36 is cylindrical with a circular cross section.

In accordance with the preferred embodiment of the invention, the reference block 2 has three reflecting surfaces at the 0° degree position of the block. One surface is a 0.125-inch-wide slot 38 machined across the bottom from left to right. Another 0.125-inch-wide slot 40 that has a depth of 0.500 inch is machined across the block from front to back. These slots form two different depth reflectors. The third depth reflector is the block's bottom surface itself, namely, base 12. In accordance with the preferred embodiment, each slot 38 and 40 is a linear groove of rectangular cross section.

To use these features, an ultrasonic probe must have access to the top (F1) and bottom (F2) focal points (centerline) of the block. The ultrasonic reference block of the preferred embodiment has a 1-inch-diameter probe access hole 4 machined across the block from left to right (as seen in FIG. 1). The top focal point F1 is located at the intersection of the block centerline and the top of access hole 4; the bottom focal point F2 is located at the intersection of the block centerline and the bottom of the access hole. The access hole is horizontal (i.e., parallel to the planar base 12), round within ±0.005 inch and contains no deviations in its roundness. The window 16 (see FIG. 2) provides viewing and access for marking the index point of each transducer in the probe being calibrated. Just below this window, a beam angle scale 42 is machined into the block for referencing.

FIG. 2 is an end view of the reference block of the invention. For long probes that require additional support, small tube sections 44a and 44b may be added to each end of the one-inch-diameter access hole 4 as shown in FIG. 3.

The first step in using the ultrasonic reference block of the invention is to determine each transducer's beam exit point, sometimes called the "center ray" or "central ray". The beam index point is the single ultrasonic ray that is closest to the exact beam angle the transducer is designed to transmit. In other words, a common 45° shear wave transducer pulsed at 2.25 MHz might produce a sound beam that incorporates angles between 37° and 48°. The 37° angle would be the trailing ray and the 48° would be the leading ray. If the transducer's piezoelectric element is mounted onto its backing material at exactly 37°, the central ray would have a beam angle of 44.8° in steel. That would be the central ray angle.

Figure 4A:
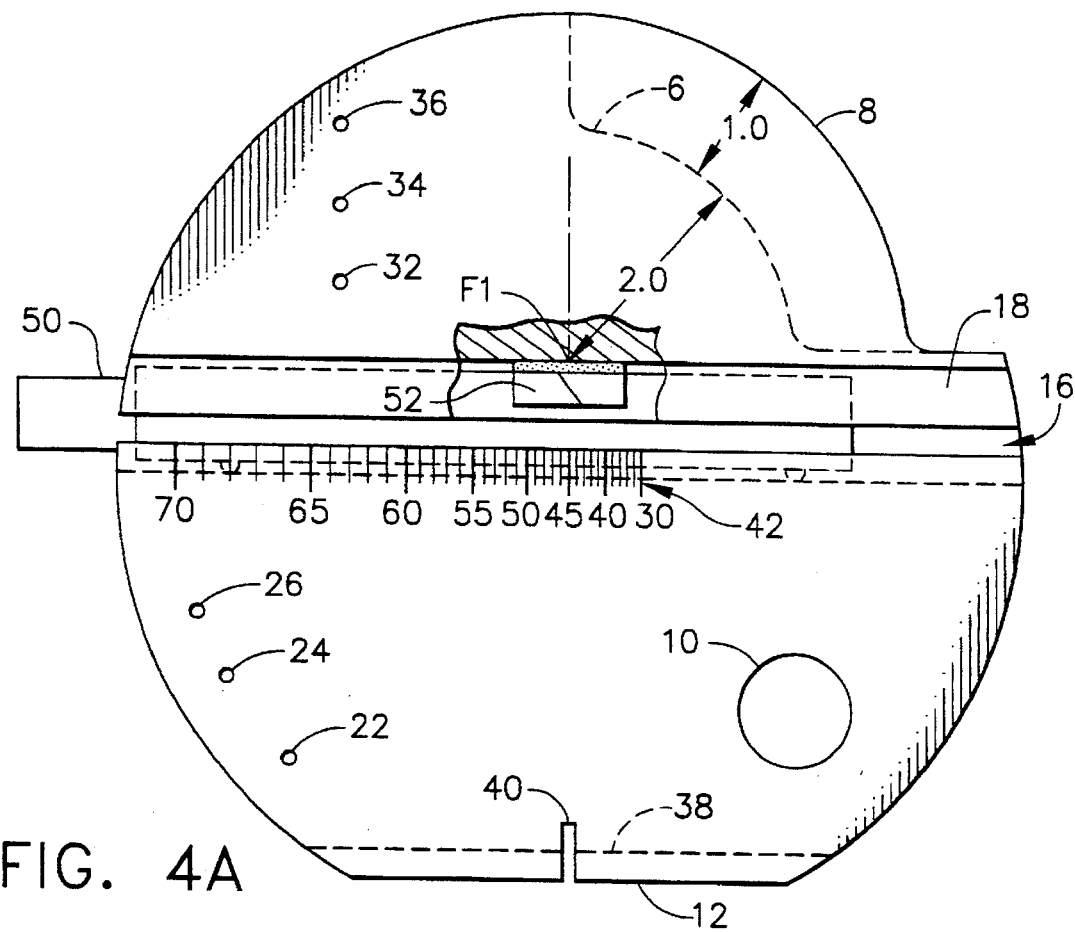
FIG. 4A is a schematic diagram showing a front view of the reference block shown in FIG. 1 with a right circular cylinder type ultrasonic probe inserted in the access hole at a position which enables sweep calibration and transducer index point determination.
Figure 4B:
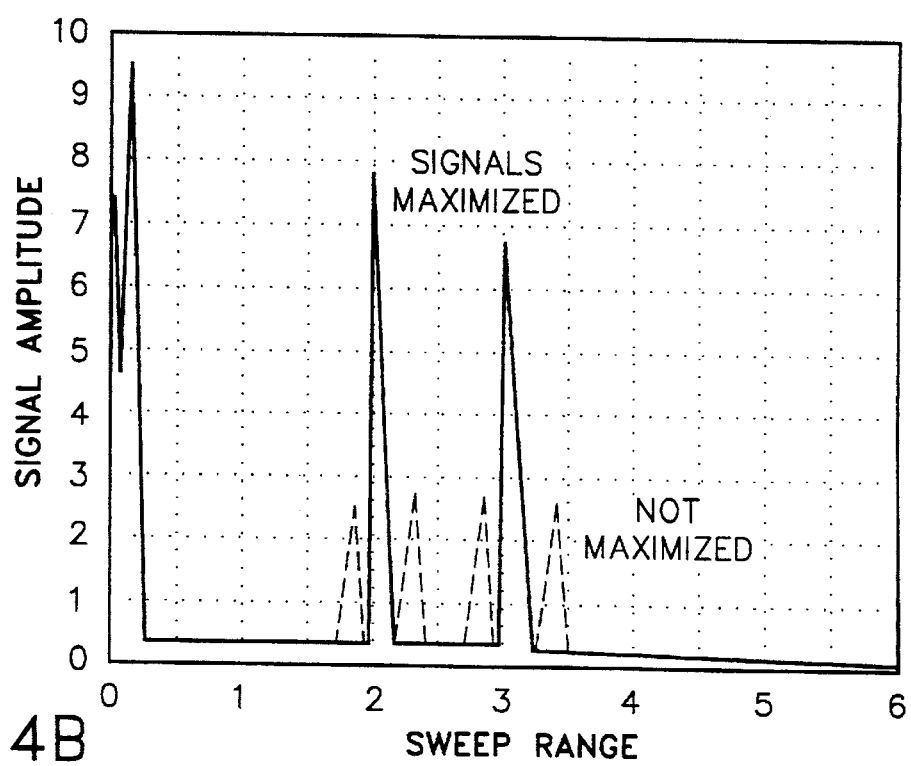
FIG. 4B is a schematic depiction of an ultrasonic instrument display of signal amplitude vs. sweep range for signals transmitted from an ultrasonic transducer positioned as shown in FIG. 4A and returned from two radii machined on the exterior of the reference block.

To determine the beam index point, the ultrasonic probe 50 is inserted into the 1-inch-diameter access hole 4 (see FIG. 4A) with the piezoelectric transducer 52 to be indexed pointing upward. The probe cable (not shown) is connected to an ultrasonic instrument (not shown). The sweep range of the instrument is calibrated by maximizing the return signals from reflecting surfaces 6 and 8. The metal path to these reflecting surfaces for a 45° angle are 2 and 3 inches respectively. The 2-inch and 3-inch radii are derived from the top focal point F1. The metal paths derived from the radii for all 45°, 60° and 70° angle beams are always set to 2 inches and 3 inches respectively on the ultrasonic instrument's display screen (or multiples thereof) when both signals are maximized simultaneously. The probe is manipulated until simultaneous maximized signals (see FIG. 4B) are obtained from the reflecting surfaces 6 and 8. Then the sweep and delay controls are adjusted until the two signals are positioned exactly at the 2- and 3-inch markers on the screen. The ultrasonic instrument's sweep range is thereby calibrated.

With the signals maximized, a line is scribed on the probe body full circumference at a point X exactly opposite the block's focal point $F_1$, i.e., where the vertical intersects the transducer. This is the transducer's index point that is used to determine beam angle and beam spread, to construct DAC curves, and to set sensitivity (gain) levels.

After determining the transducer's index point, the next step is to determine the transducer's central ray beam angle. With the probe 50 still inserted in the ultrasonic reference block 2, the probe is rotated until the transducer 52 is pointed in the downward direction and aimed at the one-inch-diameter side-drilled hole 10. The probe is moved in and out until the beam reflects from hole 10. Then the probe is manipulated until a maximized ultrasonic return signal is obtained from the one-inch-diameter side-drilled hole 10. (The signal's tip must not exceed 100% of the oscilloscope's vertical dimension to determine the signal's maximum amplitude.) The scribe line X on the probe is referenced to the nearest angle mark on the scale 42. If the scribe line X falls between degree marks, interpolation can be used to derive the center ray angle.

Figure 5A:
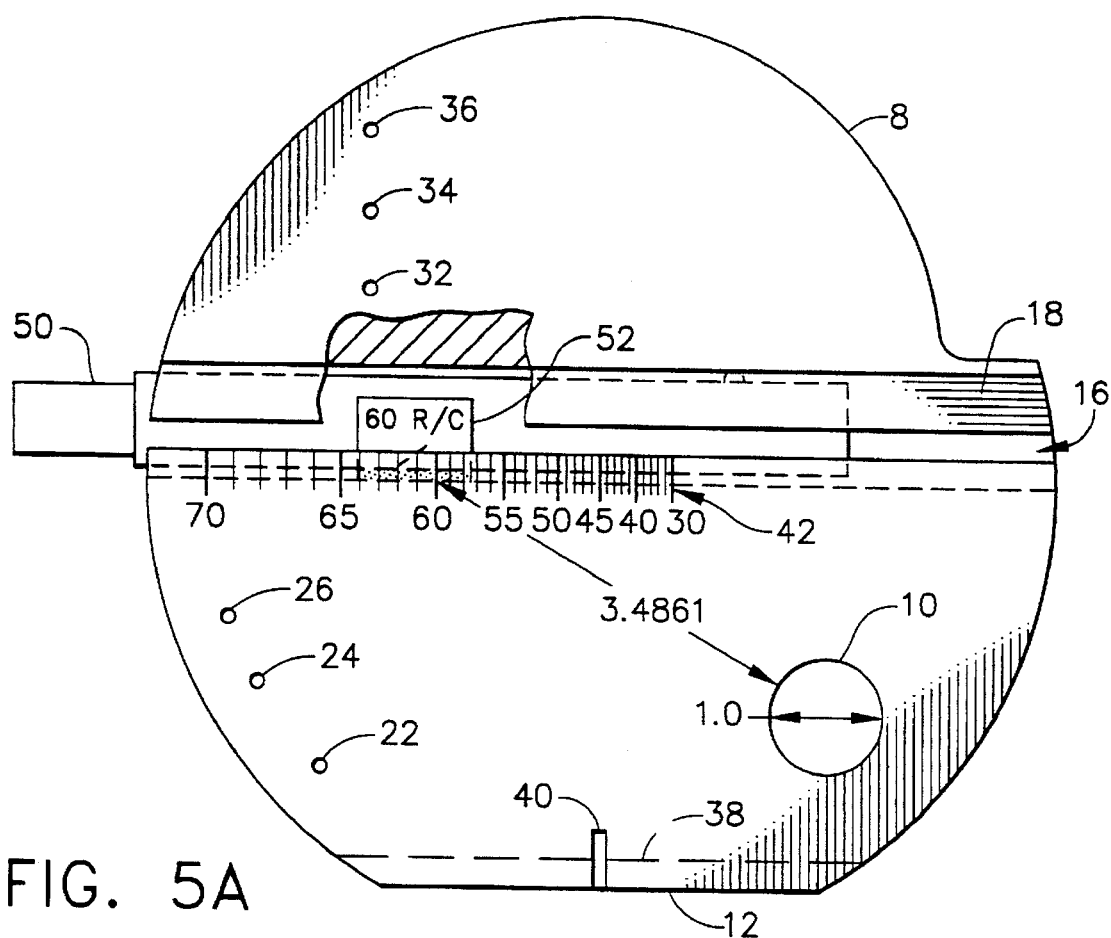
FIG. 5A is a schematic diagram showing a front view of the reference block shown in FIG. 1 with a right circular cylinder type ultrasonic probe inserted in the access hole at a position which enables individual transducer beam angle determination.
Figure 5B:
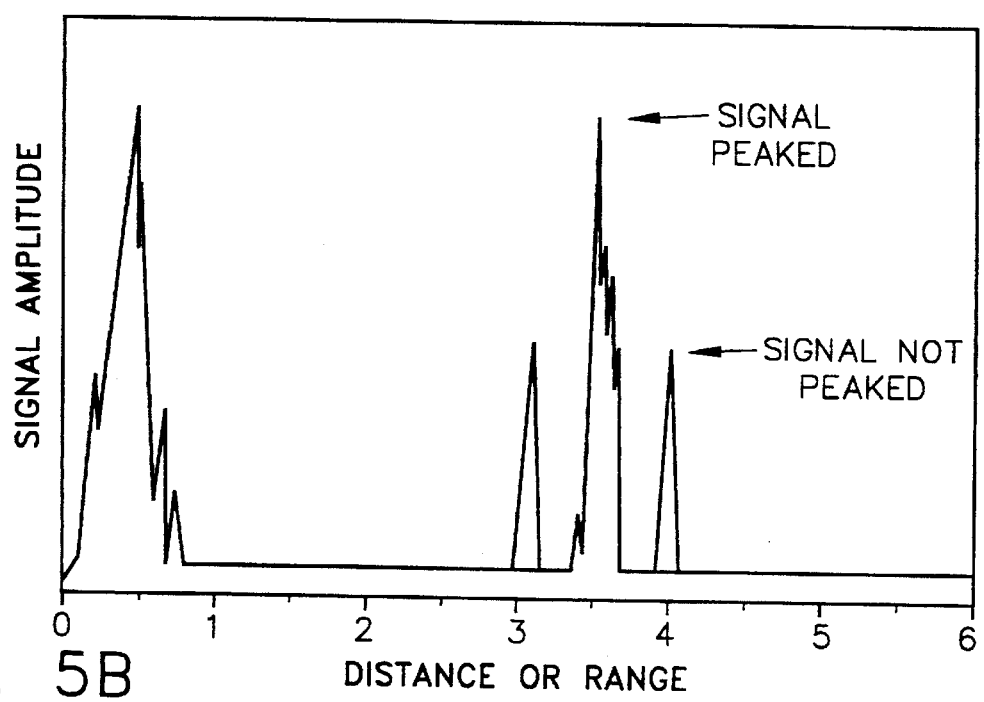
FIG. 5B is a schematic depiction of an ultrasonic instrument display of signal amplitude vs. sweep range for signals transmitted from an ultrasonic transducer positioned as shown in FIG. 5A and returned from a side-drilled circular hole in the reference block.

In FIG. 5A, a 60° refracted longitudinal wave transducer's beam is illustrated. Its central beam 46 is shown as being exactly 60° and its metal path is 3.4861 inches. A typical ultrasonic signal response is shown in FIG. 5B.

After determining a transducer center ray angle, the total beam spread at a given distance can then be derived. In this case the centers of the 0.125-inch-diameter side-drilled holes 22, 24 and 26, as shown in FIG. 3, are at a metal path of 3.5 inches from the block's bottom focal spot $F_2$. The determination of beam spread for a 60° transducer is illustrated in FIG. 6A. The central ray detects the 0.125-inch-diameter side-drilled hole 24 located at the 60° position in the block. The return signal is maximized and its amplitude is set at 80% full screen height (FSH) (see FIG. 6B). When the central ray signal is maximized, a thin pencil line is drawn on the flat surface 14 of the block immediately adjacent to the transducer's index point. The transducer is then moved backward until the signal drops to the noise level, or baseline, on the scope. This is the transducer's leading ray. Then a thin line is drawn on the block's flat surface immediately adjacent to the transducer's index point. Thereafter, the transducer is moved forward past the maximum amplitude point until the signal level again drops to the baseline noise level. This is the transducer's trailing ray. A thin line is drawn on the block's flat surface immediately adjacent to the transducer's index point. The distance between the leading ray line and the trailing ray line is then measured mechanically. This is the transducer's beam spread.

Figure 7A:
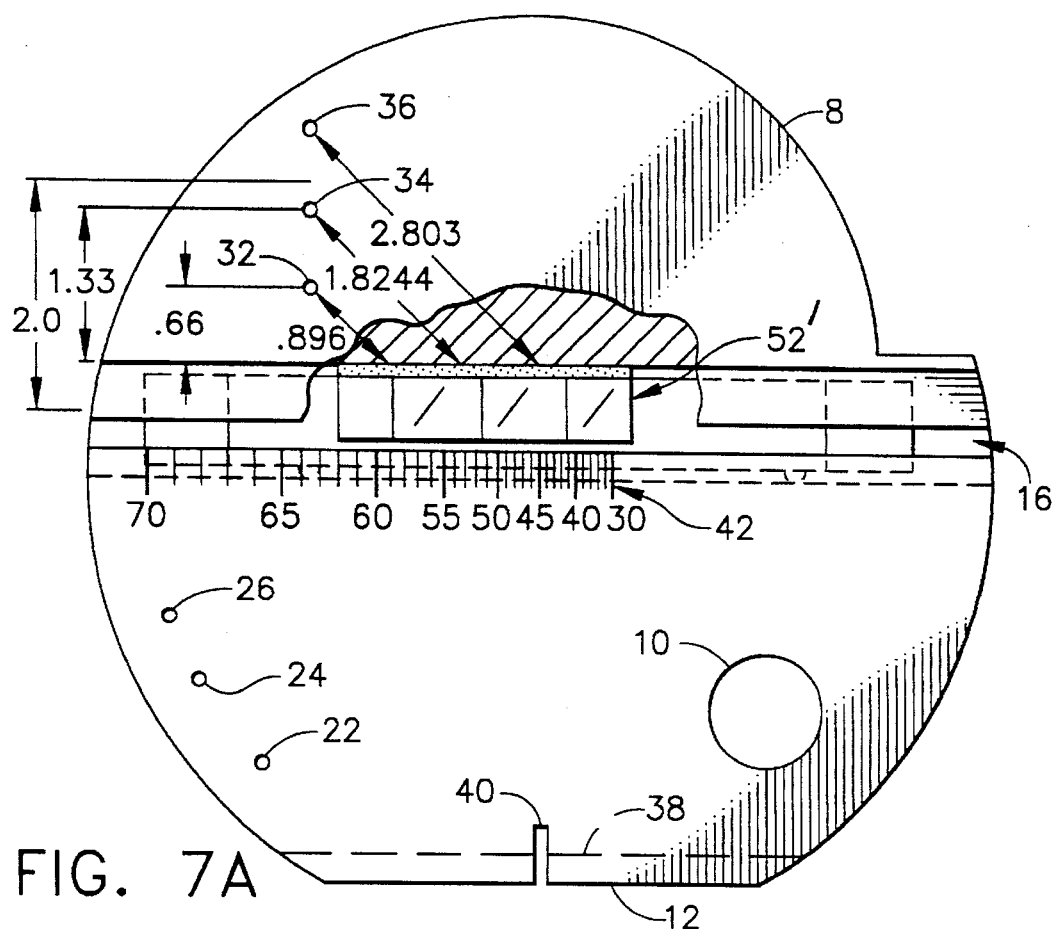
FIG. 7A is a schematic diagram showing a front view of the reference block shown in FIG. 1 with a right circular cylinder type ultrasonic probe inserted in the access hole at a position which enables distance amplitude corrected curve determination.
Figure 7B:
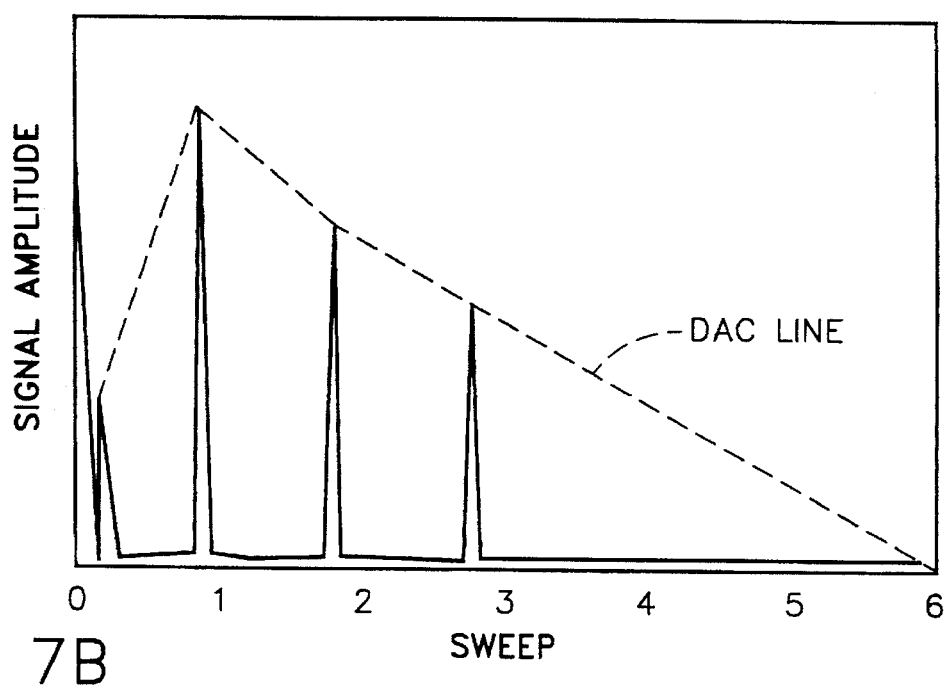
FIG. 7B is a schematic depiction of an ultrasonic instrument display of signal amplitude vs. sweep range for signals transmitted from an ultrasonic transducer positioned as shown in FIG. 7A and returned from side-drilled circular holes arranged in the reference block along a line which extends in the depth direction. The dashed lines represent a distance amplitude curve.

Distance amplitude corrected curves can be derived for angle beam search units using the reference block of the invention. Referring to FIG. 7A, a 45° transducer 52' is aimed at the aligned 0.125-inch-diameter side-drilled holes 32, 34 and 36 located above the centerline access hole 4. The ultrasonic probe 50 is manipulated until the 45° ultrasound beam reflects from the side-drilled hole 32 located 0.66 inch below the sound beam entry surface, resulting in a sound beam metal path of 0.896 inch. The return signal is maximized and its peaked tip signal is marked on the tester's screen (see FIG. 7B). The probe is then adjusted until a maximized signal is obtained from the middle-depth 34 and its tip signal is drawn on the screen. A maximized signal is then obtained from the hole 36 and its tip signal is also drawn on the screen. Then a smooth connecting line is drawn between the three tip signals and extended on both ends to encompass the entire screen, similar to that shown in FIG. 7B. This is the DAC curve. DAC curves may be used to set an inspection system's gain level prior to performing inspections on parts. Signal amplitudes from indications and flaws in the parts may be compared to these known reflector's amplitudes at any position along the curve. The inspection system's performance characteristics can be checked to verify that calibration is maintained with this reference block.

Figure 8A:
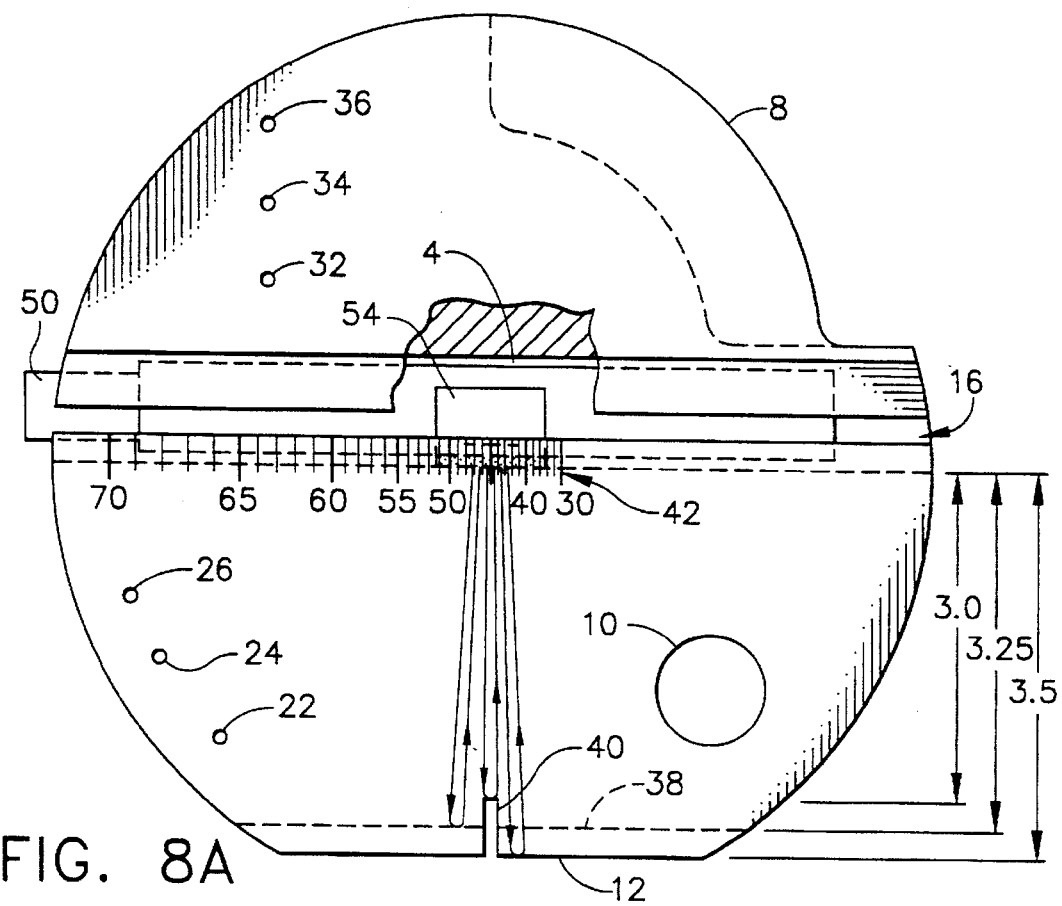
FIG. 8A is a schematic diagram showing a front view of the reference block shown in FIG. 1 with a right circular cylinder type ultrasonic probe inserted in the access hole at a position which enables evaluation of a straight-beam transducer.
Figure 8B:
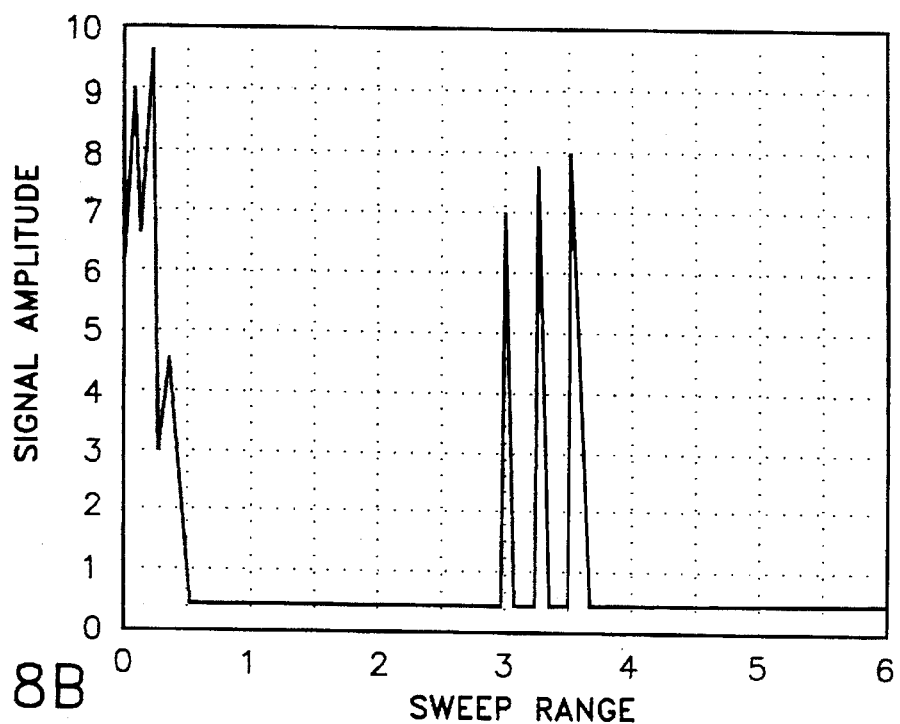
FIG. 8B is a schematic depiction of an ultrasonic instrument display of signal amplitude vs. sweep range for signals transmitted from a straight-beam transducer positioned as shown in FIG. 8A and returned from three reflecting surfaces at the 0° position of the block.

Finally, straight-beam transducers contained in right circular cylinder type ultrasonic probes can also be evaluated and calibrated using the ultrasonic reference block of the invention. A straight-beam transducer 54 and the ultrasonic instrument (not shown) can be checked for back-surface resolution by placing the transducer directly over the block's vertical centering, as shown in FIG. 8A. The straight beam ultrasound wave reflects from the three bottom surfaces 12, 38 and 40. With proper resolution, the resulting return signals should be clearly visible and separated on the oscilloscope screen, as seen in FIG. 8B, i.e., sound beam metal paths of 3.0, 3.25 and 3.5 inches should be present on the oscilloscope's screen at those positions if the instrument is calibrated. For example, a highly damped 5-MHz transducer should resolve all of the different surfaces 12, 38 and 40 and present three separate signals on the oscilloscope. The three signals should not overlap or appear as one broad jagged edged signal. A medium damped 1.0-MHz transducer would not resolve the different surfaces as well.

For use with immersion-type ultrasonic probes, the reference block of the invention is immersed in the same liquid used for coupling purposes when performing examinations in the immersed condition. For use with contact-type ultrasonic probes, the same couplant used for performing examinations is used for transducer evaluations.

The preferred embodiments of the reference block have been disclosed for the purpose of illustration. Variations and modifications of the disclosed structure will be readily apparent to practitioners skilled in the art of ultrasonic detection. All such variations and modifications are intended to be encompassed by the claims set forth hereinafter.

I claim:

1. A device for calibrating an ultrasonic transducer of a probe, comprising a block of material having a planar front face, a planar rear face parallel to said front face, a circular cylindrical access hole having a centerline axis which is parallel to said front face, and an open window extending in parallel with said access hole and providing access to said access hole from said front face, and means for reflecting ultrasound waves transmitted from a focal point in said block back to said focal point.

2. The device as defined in claim 1, wherein said ultrasound reflecting means comprise first and second reflecting surfaces in a first quadrant of said block, said first and second reflecting surfaces extending between said front and rear faces in a direction perpendicular to said front face and having first and second radii of curvature, respectively, as measured from a first focal point located at a top of said access hole, said first radius of curvature being different than said second radius of curvature, said first and second reflecting surfaces being sections of circular cylinders having a common axis of curvature.

3. The device as defined in claim 2, wherein said ultrasound reflecting means comprise a planar base perpendicular to said front and rear faces, and a first linear groove which extends parallel to said planar base and has a first predetermined depth in a direction perpendicular to said planar base.

4. The device as defined in claim 3, wherein said ultrasound reflecting means further comprise a second linear groove which extends parallel to said planar base and has a second predetermined depth in said direction perpendicular to said planar base, wherein said first predetermined depth is different than said second predetermined depth.

5. The device as defined in claim 4, wherein said first linear groove extends perpendicular to said front face and said second linear groove intersects said first linear groove at right angles.

6. The device as defined in claim 2, wherein said ultrasound reflecting means further comprise a first cylindrical hole in a second quadrant of said block, said first cylindrical hole extending between said front and rear faces in a direction perpendicular to said front face.

7. The device as defined in claim 6, wherein said ultrasound reflecting means further comprise second, third and fourth cylindrical holes in a third quadrant of said block, said second, third and fourth cylindrical holes extending between said front and rear faces in a direction perpendicular to said front face and having centers arranged along an arc having a predetermined radius measured from a second focal point located at a bottom of said access hole.

8. The device as defined in claim 4, wherein said ultrasound reflecting means further comprise fifth, sixth and seventh cylindrical holes in a fourth quadrant of said block, said fifth, sixth and seventh cylindrical holes extending between said front and rear faces in a direction perpendicular to said front face, said fifth, sixth and seventh cylindrical holes having centers arranged along a line substantially perpendicular to said centerline axis of said access hole.

9. The device as defined in claim 1, wherein a portion of said front face of said block lying immediately adjacent to said open window has a multiplicity of marks spaced to form a scale.

10. The device as defined in claim 1, wherein said ultrasound reflecting means comprise a planar base perpendicular to said front and rear faces, and a first linear groove which extends parallel to said planar base and has a first predetermined depth in a direction perpendicular to said planar base.

11. The device as defined in claim 10, wherein said ultrasound reflecting means further comprise a second linear groove which extends parallel to said planar base and has a second predetermined depth in said direction perpendicular to said planar base, wherein said first predetermined depth is different than said second predetermined depth.

12. The device as defined in claim 11, wherein said first linear groove extends perpendicular to said front face and said second linear groove intersects said first linear groove at right angles.

13. The device as defined in claim 1, further comprising a tube section having an end connected to said block, said tube section being coaxial with said access hole and having a diameter not less than the diameter of said access hole.

14. A device for calibrating an ultrasonic transducer of a right circular cylinder type probe, comprising a block of material having a planar front face, a planar rear face parallel to said front face, a planar base perpendicular to said front and rear faces, a concave circular cylindrical section which has a radius of curvature slightly greater than a radius of the probe, said concave circular cylindrical section having a centerline axis which is parallel to said base and to said front face and having a focal point along said centerline axis, and a first slot of constant depth extending substantially perpendicular to said planar base, said first slot forming a first planar ultrasonic wave reflecting surface which extends parallel to said planar base to a first depth from said planar base, said first ultrasonic wave reflecting surface being disposed to reflect ultrasound waves transmitted from said focal point back to said focal point.

15. The device as defined in claim 14, further comprising a second slot of constant depth extending substantially perpendicular to said planar base, said second slot forming a second planar ultrasonic wave reflecting surface which extends parallel to said planar base to a second depth from said planar base, said second depth being different than said first depth, said second ultrasonic wave reflecting surface being disposed to reflect ultrasound waves transmitted from said focal point back to said focal point.

16. The device as defined in claim 15, wherein said first slot extends substantially perpendicular to said front face.

17. The device as defined in claim 15, wherein said first slot extends substantially parallel to said front face.

18. A device for calibrating an ultrasonic transducer of a right circular cylinder type probe, comprising a block of material having a planar front face, a planar rear face parallel to said front face, a planar base perpendicular to said front and rear faces, a concave circular cylindrical section which has a radius of curvature slightly greater than a radius of the probe, said concave circular cylindrical section having a centerline axis which is parallel to said base and to said front face and having a focal point along said centerline axis, and a first linear ultrasonic wave reflecting interface which extends parallel to said base at a first predetermined elevation above said planar base, said first linear ultrasonic wave reflecting interface being disposed to reflect ultrasound waves transmitted from said focal point back to said focal point, wherein said block has a second linear ultrasonic wave reflecting interface which extends parallel to said base at a second predetermined elevation above said planar base, said second linear ultrasonic wave reflecting interface being disposed to reflect ultrasound waves transmitted from said focal point back to said focal point, and said first predetermined elevation being different than said second predetermined elevation.

19. The device as defined in claim 18, wherein said first linear interface extends perpendicular to said front face and said second linear interface extends parallel to said front face.

20. The device as defined in claim 19, wherein each of said first and second linear interfaces is planar and parallel to said planar base.

* * * * *